United States Patent [19]

Woehr

[11] 3,996,112
[45] Dec. 7, 1976

[54] DISTILLATION OF HEXAHALOCYCLOPENTADIENE

[75] Inventor: George C. Woehr, Buffalo, N.Y.

[73] Assignee: Hooker Chemicals & Plastics Corporation, Niagara Falls, N.Y.

[22] Filed: Apr. 15, 1974

[21] Appl. No.: 461,054

Related U.S. Application Data

[63] Continuation-in-part of Ser. No. 194,460, Nov. 1, 1971, abandoned.

[52] U.S. Cl. .................. 203/38; 424/352; 260/648 C; 203/74
[51] Int. Cl.[2] .......................................... B01D 3/34
[58] Field of Search ............. 203/29, 36–38, 203/80; 260/648 L, 648 R, 563 R, 583 B, 551 R, 623 D; 424/352

[56] References Cited

UNITED STATES PATENTS

| | | | |
|---|---|---|---|
| 2,752,297 | 6/1956 | Kleiman | 260/648 C |
| 2,945,893 | 7/1960 | Steinhofer | 260/648 C |
| 3,356,725 | 12/1967 | McBee | 260/563 R |

Primary Examiner—Norman Yudkoff
Assistant Examiner—J. Sofer
Attorney, Agent, or Firm—Peter F. Casella; James F. Mudd; David A. Stein

[57] ABSTRACT

Ultra high purity hexachlorocyclopentadiene is obtained by a two-stage distillation procedure, in the first stage of which crude hexachlorocyclopentadiene is distilled to separate hexachlorobutadiene as a distillate and in the second stage, ultra high purity hexachlorocyclopentadiene is obtained as a distillate fraction and octachlorocyclopentene is obtained as a distillation residue.

22 Claims, 1 Drawing Figure

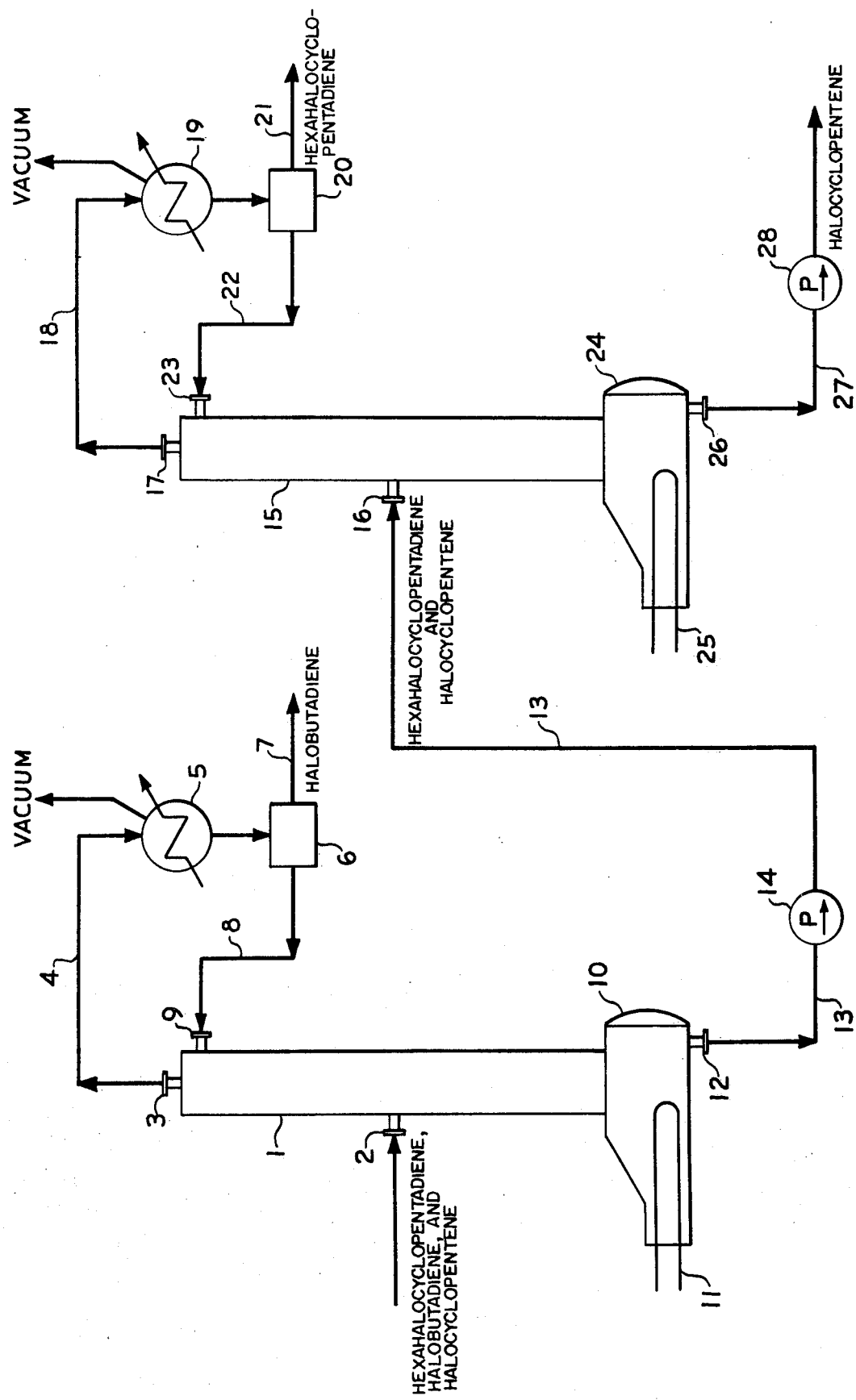

DISTILLATION OF HEXAHALOCYCLOPENTADIENE

REFERENCE TO PRIOR APPLICATION

This is a continuation-in-part of copending application Ser. No. 194,460, filed Nov. 1, 1971 and now abandoned.

This invention relates to the purification of halocyclopentadienes. More particulary it relates to a two-stage fractional distillation process for the production of ultra high purity hexachlorocyclopentadiene.

BACKGROUND OF THE INVENTION

Halocyclopentadienes, and particularly hexachlorocyclopentadienes, are useful compounds for the preparation of DielsAlder adducts. For example, the adduct with maleic anhydride, commonly known as chlorendic anhydride is useful in the preparation of polyester resins. The adduct with furan gives products which are useful as fire-retardant additives to many otherwise flammable resins.

Commercial grades of hexachlorocyclopentadiene contain impurities such as hexachlorobutadiene and octachlorocyclopentene, neither one of which will adduct with dienophiles such as maleic anhydride. These chlorocarbon impurities, as well as impurities arising from incomplete reaction give rise to objectionable odors and vapors which may attack and irritate the eyes and sensitive membranes of the respiratory tract of workers handling this material. The chlorocarbon impurities also act as skin irritants giving rise to a type of dermatitis. Moreover the chlorocarbon impurities can also form objectionable and resinous discolorations and decomposition products on subsequent reaction of the adducts with polyols and the like. The chlorocarbon impurities further, may cause corrosion damage to the metal processing equipment if allowed to remain in the hexachlorocyclopentadiene or adducts prepared therefrom.

The prior art accomplished only partial removal of these contaminants from the commercial product by various methods including one-stage fractional distillation, and by extensive recrystallization of the adducts. Moreover, these methods are time consuming and expensive and not economically adapted to a commercial operation.

In U.S. Pat. No. 3,214,444 it has been proposed to purify chlorendic anhydride and related compounds by azeotropic distillation of the halocarbon impurities wherein a material which will form a constant minimum boiling mixture with the halocarbon impurities is added to the crude anhydride and subsequently distilling off said constant minimum boiling mixture at a temperature low enough to prevent unwanted by-products from forming in the anhydride product. This method while suitable for chlorendic anhydride, is not adaptable to the purification of hexachlorocyclopentadiene and related compounds.

OBJECTS OF THE INVENTION

It is therefore a principle object of the present invention to provide an effective and economical process for the purification of halocyclopentadienes.

Another object is to provide a process for the purification of hexachlorocyclopentadiene which can be operated in a continuous manner.

Other objects will be obvious from the following description of the present invention.

SUMMARY OF THE INVENTION

Ultra high purity hexahalocyclopentadienes, i.e., material containing less than about 0.5 weight percent, and preferably less than 0.1 weight percent of halocarbon impurities, are obtained by a two-stage fractional distillation procedure which comprises:

a. distilling a crude halocyclopentadiene in a first distillation zone separating the crude into a low boiling impurities overhead fraction and partially purified halocyclopentadiene as a high boiling bottom fraction, and b. distilling said bottom fraction from the first zone in a second distillation zone separating from said bottom fraction, ultra high purity halocyclopentadiene as an overhead fraction and the high boiling impurities as still bottoms.

Preferably the distillation procedure is carried out in a continuous manner and under subatmospheric pressure.

DETAILED DESCRIPTION OF THE INVENTION

In accordance with the present invention ultra high purity hexachlorocyclopentadiene, i.e., material which is at least 99.7 percent by weight pure, is produced by a process which comprises the steps of:

a. distilling a crude hexachlorocyclopentadiene in a first fractional distillation zone containing at least ten and preferably twelve or more theoretical plates, and separating therefrom, an overhead distillate fraction containing substantially all of the hexachlorobutadiene, and a bottom fraction comprising a mixture of hexachlorocyclopentadiene and octachlorocyclopentene, and b. distilling said bottom fraction from step a in a second fractional distillation zone containing at least seven and preferably 9 or more theoretical plates and separating therefrom ultra-high purity hexachlorocyclopentadiene as a overhead distillate fraction and a still bottom fraction comprising octachlorocyclopentene.

Preferably the process is operated in a continuous manner wherein crude hexachlorocyclopentadiene is continuously fed into a first distillation column, the still bottom fraction from said first column being continuously removed and fed into a second distillation column.

The process is carried out under subatmospheric pressure, i.e., pressures within the range of from about 10 to about 300 mm Hg absolute and especially from about 20 to about 50 mm Hg. absolute, said pressures being measured at the top of each of the columns.

The first column should be operated using a relatively high reflux ratio, that is, a major amount of the liquid condensed in the top portion of the column should be returned to the column as reflux. Reflux ratios of at least 10 to 1 and preferably 40 to 1 or greater should be used.

The second column should be operated with a reflux ratio within the range of about 0.2 to 1 and 1 to 1 and preferalby about 0.5 to 1.

The columns should be constructed of materials which are resistant to corrosion. Acid resistant stainless steels, nickel, monel, and the like are suitable metals.

The columns can be of varied design. That is they may contain bubble cap trays or ceramic or metal packings. Conveniently one inch ceramic saddles can be used.

While the process of the invention has been specifically described with respect to hexachlorocyclopentadiene, it is applicable to other halocyclopentadienes, particularly hexahalocyclopentadienes of the formula

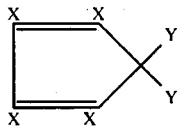

wherein X is chlorine, bromine, or fluorine and Y is chlorine, bromine or fluorine. Typical compounds are hexabromocyclopentadiene, tetrachloro-5,5-difluorocyclopentadiene, and the like.

A combination schematic and flow sheet illustrating the process of this invention is shown in the drawing attached hereto. As shown thereon, the crude mixture to be purified is fed to a first fractionating column 1, at the inlet 2. The crude mixture is separated into an overhead fraction and a bottom fraction. The former exits from the column through outlet 3, passing through pipe 4, through condenser 5, into weir 6, wherein the condensed stream is split into forward flow and reflux flow. The forward flow passes through pipe 7, into a suitable collection vessel, not shown. The reflux passes through pipe 8, back to column 1, through inlet 9.

The bottoms fraction flows into reboiler 10 containing heating means 11, and leaves the column through exit 12, flowing through pipe 13, containing pumping means 14, into the second fractionating column 15, through inlet 16. The mixture fed to the column 15, is separated therein into an overhead fraction and a bottoms fraction. The overhead fraction leaves the column through exit 17 and flows through pipe 18, through condenser 19, into weir, 20, wherein the condensed overhead fraction is split into a forward or product fraction and reflux fraction. The product fraction is directed through pipe 21, into a suitable collection vessel, not shown, while the reflux flows through pipe 22 back into column 15 at inlet 23.

The bottoms fraction flows from column 15, into reboiler 24, containing heating means 25, and exit 26, through which the high boiling residue flows through pipe 27, containing pump 28, into a suitable collection vessel, not shown.

As is known, halocyclopentadienes may be prepared by the halogenation of cyclopentadiene. As prepared, the crude product usually contains residual amounts of hydrohalic acids and free halogen. Prior to distillation of the crude halocyclopentadienes in accordance with this invention, it is preferred that the crude material be pretreated to remove these acid and halogen impurities. For example, hydrogen chloride and chlorine gas may be removed from crude hexachlorocyclopentadiene by heating the crude material to about 135° centigrade and treating the crude with a stream of nitrogen or other inert gas.

It is known also that the chlorination of cyclopentadiene may be carried out in the presence of a catalyst, such as iron and/or aluminum chloride. Residues of these catalyst which may be present in the crude hexachlorocyclopentadiene are preferably removed prior to fractional distillation by treatment of the crude product with small amounts e.g., 0.1 percent by weight or less of a metal oxide such as a Group IIA metal oxide, such as calcium oxide, magnesium oxide, or barium oxide.

The halocyclopentadienes, and particularly hexachlorocyclopentadiene, are sensitive to oxygen, being relatively readily oxidized to ketones, such as hexachlorocyclopent-3-enone and hexachlorocyclopent-3-enone. It has been found by another inventor that such ketonic derivatives can be effectively can be effectively removed by treating the crude material with a substance which reacts with ketones to form solid derivatives which can be separated from the liquid mass by, for example, filtration. Substances such as ammonia, amine derivatives such as phenyl hydrazine, semicarbazone and the like, hydroquinones, such as toluhydroquinone can be used to remove ketones from the crude halocyclopentadienes. It is preferred to treat the crude halocyclopentadiene prior to fractional distillation with a substance which will react with ketonic impurities to form solid derivatives. It is especially preferred to treat the crude halocyclopentadienes with ammonia prior to final purification by fractional distillation in accordance with this invention. Ammonia is the preferred treatment agent since it is relatively efficient and additionally removes not only ketonic impurities but also insolubilizes metal catalyst residues such as aluminum chloride.

Following removal of the ketonic impurities the treated material should be handled and maintained in an oxygen free atmosphere to prevent further formation of ketones.

The following examples will illustrate the process of the present invention. In this specification and claims, parts and percentages are by weight and temperatures are given in degrees centigrade unless otherwise specified.

EXAMPLE 1

REMOVAL OF KETONES FROM CRUDE HEXACHLOROCYCLOPENTADIENE.

Anhydrous ammonia was passed through 850 parts of crude hexachlorocyclopentadiene at about 35°, at the rate of 0.03 parts of ammonia for 30 minutes and at the rate of 0.033 parts of ammonia for 210 minutes. A total of 7.8 parts of ammonia was introduced. In the off gas from the treatment vessel, 4.9 parts of ammonia were detected. Accordingly about 2.9 parts of ammonia were consumed in this treatment. The treated hexachlorocyclopentadiene contained a modest amount of off white solids suspended therein and the mass had a Gardner color of 5½. The treated material was filtered and the filtrate was distilled in a vacuum of about 25 mm Hg pressure through a one foot Vigreau column to obtain hexachlorocyclopentadiene having a color of 5. The residue, containing a large amount of black solids had a color of about 16. No hexachlorocyclopent-2-enone could be detected by gas chromatography analysis in the distillate fraction.

Repetition of the above treatment process but at 140° and in which ammonia gas at the rate of 0.3 parts per minute were passed through the crude material for 30 minutes gave analogous results. Thus 9 parts of ammonia were charged and 8 parts of ammonia gas were detected in the off gas, indicating that one part of ammonia was consumed in this treatment. The treated product contained 0.05 part of a white solid, and had a color of 5½. The distilled product contained no detectable (by gas chromatography analysis) amount of ketones.

EXAMPLE 2

TWO-STAGE FRACTIONAL DISTILLATION OF CRUDE HEXACHLOROCYCLOPENTADIENE.

Crude hexachlorocyclopentadiene, which had been freed of chlorine and hydrogen chloride by heating at about 135° in a stream of nitrogen gas and thereafter treated with about 0.04 percent of magnesium oxide to remove iron and aluminum chloride residues was continuously fed to fractionating column having 12 theoretical plates. The column, 60 inches in diameter, was packed to 45 feet height with one inch ceramic saddles.

The feed stock to this column was made at the rate of about 5633 parts per hour and had the following average composition

| | |
|---|---|
| Perchloroethylene | 8.5 parts |
| Hexachlorobutadiene | 56.5 parts |
| Hexachlorocyclopentadiene | 5343.0 parts |
| Octachlorocyclopentene | 225.0 parts |

The column operated under 35 mm Hg absolute pressure measured at the top of the column. The overhead (temperature of 132°) taken from the top of the column, at the rate of 15,888 parts per hour was condensed and passed through a weir and split into 15,557 parts per hour of condensate which was returned to the column as reflux and 331 parts per hour of overhead product (reflux ratio of 47/1) having a composition of

| | |
|---|---|
| Perchloroethylene | 8.5 parts |
| Hexachlorobutadiene | 55.5 parts |
| Hexachlorocyclopentadiene | 267.0 parts |

The bottoms fraction of this column flowed from the bottom into a reboiler operated at about 168° under 110 mm Hg pressure and was pumped at the rate of 5302 parts per hour into a second column. This bottom fraction had the following average composition

| | |
|---|---|
| Hexachlorobutadiene | 1.0 part |
| Hexachlorocyclopentadiene | 5076.0 parts |
| Octachlorocyclopentene | 225.0 parts |

This second column was 42 inches in diameter and was packed for 35 feet of its height with 1 inch ceramic saddles. This column operated with nine theoretical plates.

Overhead material emanated from the top of the second column at 136° under 35 mm Hg pressure at the rate of 7410 parts per hour, which was condensed and passed through a weir and split into a product fraction having the composition

| | |
|---|---|
| Hexachlorobutadiene | 1.0 part |
| Hexachlorocyclopentadiene | 4938.0 parts |
| Octachlorocyclopentene | 1.0 part | and a reflux fraction which was returned to the column at the top thereof. The column operated at a reflux ratio of about 0.5/1.

The bottoms fraction passed through a reboiler operating at 100 mm Hg and 183° before being exited at the rate of 362 parts per hour. The bottoms fraction had the average composition of

| | |
|---|---|
| Hexachlorocyclopentadiene | 138.0 parts |
| Octachlorocyclopentene | 224.0 parts |

It can be seen that the product obtained from this two stage distillation procedure was ultra high purity hexachlorocyclopentadiene, being 99.96 percent pure.

A crude hexachlorocyclopentadiene mixture which had been pretreated with ammonia, as described in Example 1 above, to remove ketonic impurities, degassed to remove chlorine and hydrochloric acid, and treated with magnesium oxide to remove residues, was distilled as described in this Example to produce an ultra high purity hexachlorocyclopentadiene product.

EXAMPLE 3

In a similar manner to that described in Example 2, above, crude hexachlorocyclopentadiene, having the composition

| | |
|---|---|
| Perchloroethylene | 8.4 parts |
| Hexachlorobutadiene | 56.2 parts |
| Hexachlorocyclopentadiene | 5331.0 parts |
| Octachlorocyclopentene | 224.8 parts | was fed into a first fractionating column having 10 theoretical plates, being 38 inches in diameter and packed for 35 feet in height with one inch ceramic saddles.

Overhead material at the rate of 5789 parts per hour was taken off at 132° and 35 mm Hg pressure from the top of the column and split into one part of forward flow having the composition

| | |
|---|---|
| Perchloroethylene | 8.4 parts |
| Hexachlorobutadiene | 46.2 parts |
| Hexachlorocyclopentadiene | 267.0 parts | and 17 parts of reflux which were returned to the top of the column.

The bottom fraction flowed through a reboiler operated at 168° under 100 mm Hg at the rate of 5298.8 parts per hour having the composition

| | |
|---|---|
| Hexachlorobutadiene | 10.0 parts |
| Hexachlorocyclopentadiene | 5064.0 parts |
| Octachlorocyclopentene | 224.8 parts |

This bottom fraction was pumped to a second fractionating column having the dimensions of 42 inches in diameter, packed to 30 feet height with one inch ceramic saddles and operated with the equivalent of seven plus theoretical plates.

The overhead fraction taken from the top of this column at 135° and 35 mm Hg pressure, at the rate of 7410 parts per hour was split into 1 part reflux and 2 parts forward (product) fraction. The latter had the composition

| | |
|---|---|
| Hexachlorobutadiene | 10 parts |
| Hexachlorocyclopentadiene | 4927.5 parts |
| Octachlorocyclopentene | 2.5 parts |

The bottoms fraction from this second column exited into a reboiler operating at 100 mm Hg pressure and 183°. The bottoms fraction exited from the reboiler at the rate of 358.8 parts per hour with the composition of

| | |
|---|---|
| Hexachlorocyclopentadiene | 136.5 parts |
| Octachlorocyclopentene | 222.3 parts |

It can be seen that the hexachlorocyclopentadiene product obtained in this manner had a purity of 99.75 weight percent.

This invention has been described and illustrated by means of certain preferred embodiments. As will be apparent to those skilled in the art of this invention variations in the details disclosed herein can be made without departing from the scope and spirit of the invention.

I claim:

1. The process for preparing ultra high purity hexahalocyclopentadiene containing less than about 0.5 weight percent of halocarbon impurity from a crude hexahalocyclopentadiene mixture comprising hexahalocyclopentadiene and halobutadiene, halocyclopentene and ketonic impurities which comprises:
   1. pretreating said crude hexahalocyclopentadiene mixture to remove said ketonic impurities by reacting said mixture with a member of the group consisting of gaseous ammonia, phenylhydrazine, semicarbazone and toluhydroquinone, whereby said ketonic impurities are converted to solid product,
   2. feeding the resultant pretreated mixture to a first fractional distillation zone and separating said mixture into an overhead fraction containing substantially all the halobutadiene impurity and a bottoms fraction containing a mixture of the desired hexahalocyclopentadiene and the halocyclopentene impurtiy, feeding said bottoms fraction from said first zone to a second fractional distillation zone and separating said bottoms fraction therein into an overhead product fraction consisting essentially of ultra high purity hexahalocyclopentadiene and a bottom fraction containing substantially all of the halocyclopentene impurity.

2. The process of claim 1 in which the crude halocyclopentadiene mixture is pretreated with gaseous ammonia.

3. The process of claim 1 in which the crude hexahalocyclopentadiene is crude hexachlorocyclopentadiene.

4. The process of claim 3 in which the fractional distillation process is a continuous process.

5. The process of claim 4 in which the first fractional distillation zone contains at least ten theoretical plates and the second fractional distillation zone contains at least seven theoretical plates.

6. The process of claim 5 in which the first fractional distillation zone contains twelve theoretical plates and the second fractional distillation zone contains nine theoretical plates.

7. The process of claim 5 in which the distillation is carried out under a subatmospheric pressure within the range of about 10 and about 300 mm Hg measured at the top of each zone.

8. The process of claim 7 in which the distillation portion of the process is carried out within the range of about 20 and about 50 mm Hg pressure.

9. The process of claim 1 wherein the reaction to convert ketonic impurities to solid product is carried out at a temperature of about 35° to 140° Centigrade.

10. The process of claim 9 wherein the reaction to convert ketonic impurities to solid product is carried out at a temperature of about 35° to 140° Centigrade.

11. The process for preparing ultra high purity hexahalocyclopentadiene containing less than about 0.5 weight percent of halocarbon impurity from a crude hexahalocyclopentadiene mixture comprising hexahalocyclopentadiene and halobutadiene, halocyclopentene impurities and catalyst residues which comprises:
   1. pretreating said crude hexahalocyclopentadiene mixture to remove said catalyst residues by reacting said mixture with about 0.1 percent or less weight of a Group IIA metal oxide,
   2. feeding the resultant pretreated mixture to a first fractional distillation zone and separating said mixture into an overhead fraction containing substantially all the halobutadiene impurity and a bottoms fraction containing a mixture of the desired hexahalocyclopentadiene and the halocyclopentene impurity, feeding said bottoms fraction from said first zone to a second fractional distillation zone and separating said bottoms fraction therein into an overhead fraction consisting essentially of ultra high purity hexahalocyclopentadiene and a bottoms fraction containing substantially all of the halocyclopentene impurity.

12. The process of claim 11 in which the metal oxide is magnesium oxide.

13. The process of claim 11 in which the crude hexahalocyclopentadiene is crude hexachlorocyclopentadiene.

14. The process of claim 13 in which the fractional distillation step is a continuous process.

15. The process of claim 14 in which the first fractional distillation zone contains at least ten theoretical plates and the second fractional distillation zone contains at least seven theoretical plates.

16. The process of claim 15 in which the first fractional distillation zone contains twelve theoretical plates and the second fractional distillation zone contains nine theoretical plates.

17. The process of claim 15 in which the distillation portion of the process is carried out under a subatmospheric pressure within the range of about 10 and about 300 mm Hg measured at the top of each zone.

18. The process of claim 17 in which the distillation portion of the process is carried out within the range of about 20 and about 50 mm Hg pressure.

19. The process for preparing ultra high purity hexahalocyclopentadiene containing less than about 0.5 weight percent of halocarbon impurity from a crude hexahalocyclopentadiene mixture comprising hexahalocyclopentadiene and halobutadiene, halocyclopentene, and ketonic impurities and catalyst residues which comprises:
   1. pretreating said crude hexahalocyclopentadiene mixture to remove said ketonic impurities by reacting said mixture with a member of the group consisting of gaseous ammonia, phenylhydrazine, semicarbazone and toluhydroquinone, whereby said ketonic impurities are converted to solid product, 2. treating said pretreated mixture to remove catalyst residues by reacting said pretreated mixture with about 0.1 percent or less by weight of a Group IIA metal oxide, and 3. feeding the resultant pretreated mixture to a first fractional distillation zone and separating said mixture into an overhead fraction containing substantially all the halobutadiene impurity and a bottoms fraction containing a mixture of the desired hexahalocyclopentadiene and the halocyclopentene impurity, feeding said bottoms fraction from said first zone to a second fractional distillation zone and separating said bottoms fraction therein into an overhead product fraction consisting essentially of ultra high purity hexahalocyclopentadiene and a bottoms fraction containing substantially all of the halocyclopentene impurity.

20. The process of claim 19 in which the crude hexahalocyclopentadiene mixture is a crude hexachlorocyclopentadiene mixture.

21. The process of claim 19 in which the crude hexahalocyclopentadiene mixture is pretreated with gaseous ammonia.

22. The process of claim 19 in which the metal oxide is magnesium oxide.

* * * * *